United States Patent [19]

Genese et al.

[11] Patent Number: 4,994,079

[45] Date of Patent: Feb. 19, 1991

[54] GRASPING FORCEPS

[75] Inventors: Joseph Genese, Covington; Peter Perez-Castro, Conyers, both of Ga.

[73] Assignee: C. R. Bard, Inc., Murray Hill, N.J.

[21] Appl. No.: 386,224

[22] Filed: Jul. 28, 1989

[51] Int. Cl.⁵ .............................................. A61B 17/28
[52] U.S. Cl. ......................................... 606/206; 128/6
[58] Field of Search ............... 606/140, 141, 205, 206, 606/210, 127, 128, 46, 47, 51, 52; 294/100; 128/4, 6, 7

[56] References Cited

U.S. PATENT DOCUMENTS

| | | |
|---|---|---|
| 3,958,576 | 5/1976 | Komiya ............................ 606/140 X |
| 3,989,049 | 11/1976 | Yoon . |
| 4,085,743 | 4/1978 | Yoon . |
| 4,103,680 | 8/1978 | Yoon . |
| 4,174,715 | 11/1979 | Hasson . |
| 4,226,239 | 10/1980 | Polk et al. . |
| 4,230,116 | 10/1980 | Watson . |
| 4,374,523 | 2/1983 | Yoon . |
| 4,467,802 | 8/1984 | Maslanka . |
| 4,493,319 | 1/1985 | Polk et al. . |
| 4,607,620 | 8/1986 | Storz . |
| 4,654,028 | 3/1987 | Suma . |
| 4,655,219 | 4/1987 | Petruzzi . |

Primary Examiner—Michael H. Thaler
Attorney, Agent, or Firm—Dennison, Meserole, Pollack & Scheiner

[57] ABSTRACT

A grasping forceps including a handle and an elongate cable with resiliently outwardly flared claws at the leading end thereof. The cable is of a fixed length relative to the handle. A closure sleeve surrounds the cable and is selectively manipulated from the handle, for movement to an extended position, relative to the handle, wherein the forward portion of the closure sleeve envelops and inwardly collapses all but the leading end portions of the claws. The closure sleeve in the retracted position, allowing for an outward springing of the claws into grasping position. The closure sleeve is surrounded by a sheath selectively extensible and relative to the handle and moveable to an extended position fully enclosing the closure sleeve and collapsed claws, the sheath projecting slightly forward thereof whereby the claw tips are recessed relative to the forward end of the sheath and are completely protectively enclosed thereby. The handle of the device, as well as the sheath controlling slide are of complementary rectangular configurations. Cooperating releasable interlocking elements can be provided to fix the sheath in the retracted position.

16 Claims, 4 Drawing Sheets

GRASPING FORCEPS

BACKGROUND OF THE INVENTION

1. Field of the Invention

The present invention relates to a grasping forceps for use in conjunction with endoscopic instruments, for example a ureteroscope, wherein the forceps, with an appropriate grasping distal end, extends through and is manipulated beyond the positioned instrument for capturing the target, for example, a stone, stent, clump of tissue, or the like.

Such forceps, as well as the above referred to relationship thereof to endoscopic instruments, are well known in the art and are principally intended for manual control by a single hand wherein both the thumb and fingers are used for manipulation of the functioning components.

A common form of grasping forceps utilizes three or four flexible grasping prongs or claws outwardly diverging from the end of a flexible shaft or cable and selectively retracted into grasping engagement upon telescopic retraction within a cable surrounding sleeve which inwardly biases the claws into generally coaxial alignment with the cable. However, inasmuch as the distal ends of the collapsed claws frequently remain exposed, both the claws and the interior of the scope tend to become damaged during passage of the forceps through the scope's working channel. Any such damage or disruption during a surgical procedure is clearly undesirable.

Avoidance of this problem of potential damage to both the scope and the forceps by an extension of the collapsing sleeve beyond the ends of the claws also raises significant problems. More specifically, in light of the normally sharpened and in-turned nature of the tips of the forcep claws, any complete collapsing and interengagement of these tips will result in a tendency of the tips to interlock or jam together whereby automatic opening of the claws either will not occur at all upon retraction of the collapsing sleeve, or will do so in an uneven and unpredictable manner, neither situation of which would be acceptable.

Another problem commonly encountered with known grasping forceps is the difficulty in maintaining the gripping or grasping claws, during collapsing engagement with the object, at a fixed axial location relative to the end of the scope and the target object itself. In other words, many forceps effect the closing of the claws by an axial retraction of the claws into a collapsing sleeve which results in a tendency to simultaneously retract from the target object.

SUMMARY OF THE INVENTION

The forceps of the present invention, particularly adapted for use in conjunction with ureteroscopes and the like, is constructed for introduction and manipulation through a scope in a manner which protects both the scope and the forceps against possible damage as the forceps move through the interior channel of the scope. This is achieved by a unique means of closing and enclosing the claws without affecting the complete operability thereof at the target site.

In conjunction therewith, it is a significant object of the invention to provide for the complete protective enclosure of the jaws, while moving through the scope, without locking of the jaws with the tips interengaged in a manner as might prevent a free opening of the jaws.

In achieving the above, the forceps includes a closure sleeve closely about the claw cable in conjunction with means for manipulating the closure sleeve between a retracted position rearward of the claws sufficient to allow for full resilient expansion of the claws, and a forward position telescoped over the claws a sufficient distance to effect an inward collapsing of the claws without completely enclosing the claws. Specifically, the closure sleeve terminates sufficiently rearward of the in-turned tips of the claws to bring the claws into generally coaxial alignment with the main shaft or cable body and to generally nest the tips without interlocking or jamming the tips such as might prevent free opening of the claws.

The closure sleeve is in turn surrounded by a reciprocating sheath which, in the forwardmost position thereof, encloses both the leading portion of the closure sleeve and the closed or collapsed claws, the sheath extending slightly forward of the claw tips to insure a complete protective enclosure thereof. It will be recognized that the sheath, having an internal diameter greater than the external diameter of the closure sleeve, will effectively surround and enclose the claw tips without exerting any direct closure force on the claws. Thus, the claws are completely contained and protected while the potential for disruption of the operative manipulation of the claws is avoided.

In use, the sheath is maintained fully extended for protectively enclosing the claws as the claws move through the scope, thus avoiding any potential for damage to either the scope or the claws. Once engaged through the scope, and preferably as the distal or claw end approaches the target site, the claws and the closure sleeve are allowed to advance out of the sheath, exposing the sleeve-closed claws for manipulation of the claws through an initial retraction of the closure sleeve, an engagement of the claws with the object to be grasped, and a subsequent forward extension of the closure sleeve to grasp the target object for removal with the claws.

Other objects and advantages of the invention, the specifics of which will become more apparent from the following detailed description of the invention, include the provision of forceps which allow for manipulation of the claws, during both opening and closing, in a manner whereby the axial position of the claws, that is relative to both the scope and the target object, does not change. This is significant in enabling a closing of the claws about the target object without a simultaneous retraction relative to the target object as might affect engagement therewith. Such an arrangement is basically achieved by utilizing a fixed length claw cable in conjunction with a reciprocating closure sleeve which slides thereon.

Other objects include the provision of a unique control system for single-handed manipulation of both the closure sleeve and the sheath in an ergonomically superior configuration which allows for both better control and the fabrication of very small 3 Fr. instruments.

DESCRIPTION OF PREFERRED EMBODIMENTS

Referring more specifically to the drawings the forceps 20 includes an elongate handle 22 ergonomically configured to be held and manipulated by one hand. An elongate chamber 24, defined longitudinally through the handle 22, opens through the distal end 26 of the handle. The chamber 24, at the proximal end 28 of the handle 22, is closed by a plug-type end cap 30 affixed therein and providing an end piece to the handle 22 which is peripherally coextensive therewith. Both the handle 22 and the axial chamber 24 therein are preferably of constant rectangular cross-sectional configurations to facilitate a firm non-rotational gripping of the instrument.

The handle is completed by an elongate slot 32 defined through the top wall 34 of the housing 22 along substantially the entire length thereof from the rearwardly mounted plug cap 30 to a point just rearward of the leading or distal end 26 of the handle 22 whereby an integral transverse crossbar 36 is defined. The top wall 34, longitudinally along and the opposite sides of the slot 32, extends inwardly from the respective side walls 38 of the handle 22 and defines chamber-overlying shoulders 40.

The actual gripping component of the forceps 20 comprises an elongate fixed length flexible shaft or cable 42 with a distal end comprising a gripping or grasping head 44 with triradiate claws 46. The claws 46, when unconfined, assume a forwardly diverging outwardly spread relationship with each other terminating in free gripping ends or tips 48. The claws 46, as shall be described subsequently, are capable of being resiliently laterally inwardly collapsed into general coaxial alignment with the cable. As desired, the cable can be defined by separately wound wires each terminating in one of the aforesaid claws. Alternatively, the cable can be of a single extrusion with the claws defined therefrom.

The shaft or cable 42 extends longitudinally through the hollow handle 22 and both through and for a substantial extent beyond the open forward end 26 thereof. The proximal end 50 of the cable 42 is received centrally within the end plug 30 through a vertical slot 52 and is fixed therein by appropriate set screw means 54 threaded inward through the upper end of the plug 30 immediately outward of the near or proximal end of the handle 22. The cable 42, and hence the gripping head 44 is thus longitudinally fixed relative to the handle 22, with the cable 42 extending generally axially through the handle.

The opening and closing of the claws 46 are effected utilizing a closure sleeve 56, preferably formed of stainless steel for maximum strength and flexibility, and resistance to developing kinks as might weaken or otherwise affect the operation of the sleeve. The sleeve 56 is closely received about the cable 42 for longitudinal reciprocation thereon relative to the gripping head 44.

Longitudinal reciprocation of the closure sleeve is controlled by a thumb-manipulating control knob 58 which extends through and is guided for longitudinal movement along the elongate slot 32. The control knob 58 includes an outer portion 60, configured for a non-slipping engagement by the thumb of the user, which transversely spans the slot 32 and overlies the top wall 34 of the handle 22 to the opposite sides of the slot. The knob also includes an inner or lower block-like body portion 62 received within the handle chamber 24 and defining a pair of upwardly directed opposed side ledges 64 which engage beneath the opposed shoulders 40 defined by the top wall 34 to the opposite sides of the slot 32. The knob 58 is thus confined to movement solely axially relative to the handle 22.

A mounting tube 66 of slightly greater length than the knob 58 is longitudinally received through and fixedly secured within the lower portion 62 of the knob 58. The closure sleeve 56 is in turn longitudinally received through the mounting tube 66 and fixedly secured therein, for example by swaging the leading end of the tube 66 and/or by adhesive. The use of the relatively rigid tube 66 assures a proper locking engagement of the highly flexible closure sleeve to the control knob 58.

Figures 1, 9, 10, 15:
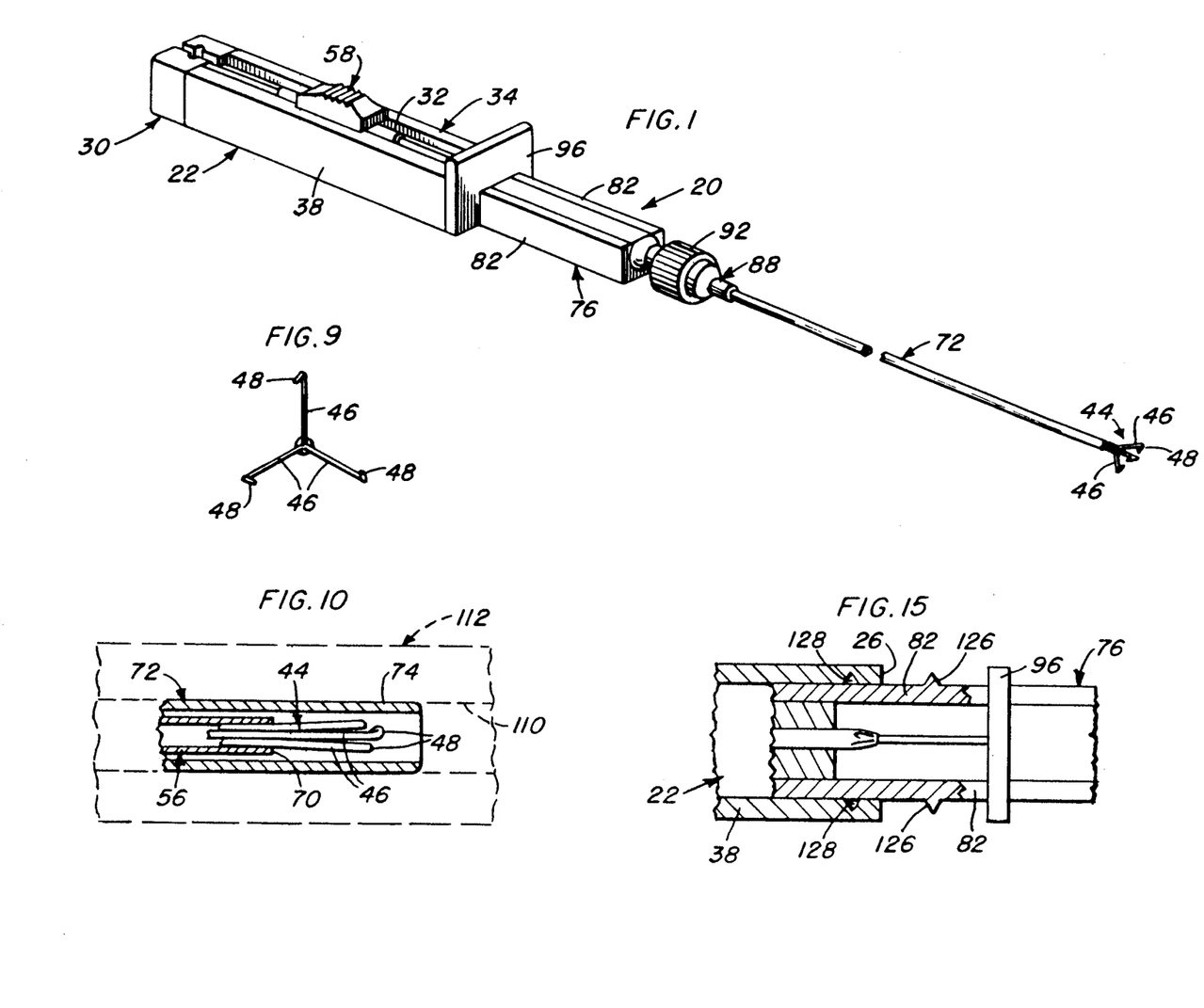
FIG. 1 is a perspective view of the grasping forceps of the invention with the claws extended or opened.
FIG. 9 is a front elevational view of the open claws.
FIG. 10 is an enlarged cross-sectional detail taken substantially on a plane passing along 10—10 in FIG. 2.
FIG. 15 illustrates a further exemplary means of fixing the sheath in a predetermined position.
Figure 3:
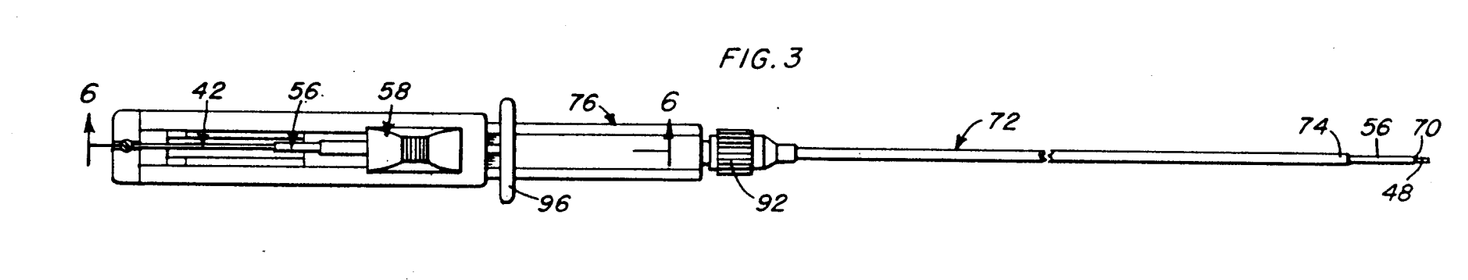
FIG. 3 is a similar top plan view with the sheath retracted.
Figure 4:
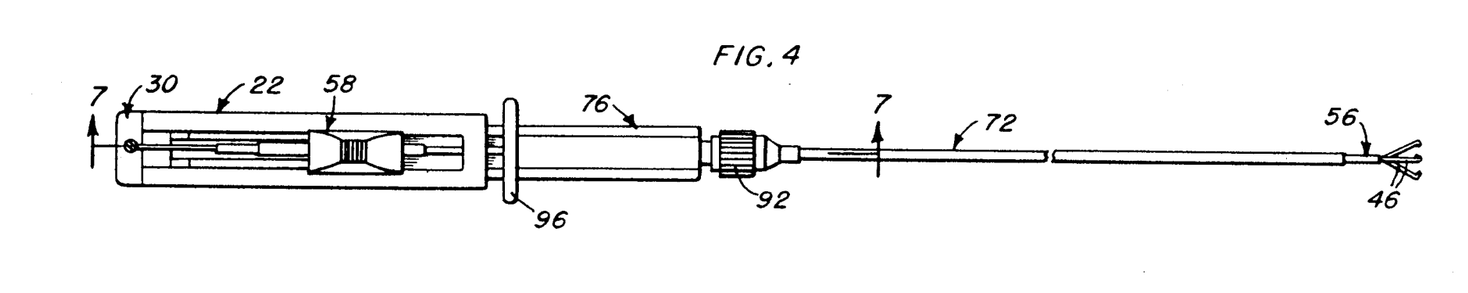
FIG. 4 is a similar top plan view with the closure sleeve retracted and the claws open.

The closure sleeve 56, in the forwardmost position thereof, as best noted in FIGS. 3, and 10, has the distal end 70 thereof extended sufficiently forward over the claws 46 to effect an inward collapsing of the claws into general axial alignment with the main cable or shaft 42, while at the same time terminating short or rearward of the extreme tips 48 of the claws. This is particularly significant in that in view of the close-tolerance engagement of the sleeve 56 over the cable 42 and the claws 46 as the closure sleeve 56 is forwardly moved to effect the closing of the claws 46, and in light of the in-turned, overlapping and possibly sharp nature of the claw tips 48, any extension of the closure sleeve 56 beyond a forward position sufficient so as to collapse the claws 46 into substantially alignment with the main cable 42, and, in particular movement of the closure sleeve 56 to completely enclose the tips 48, results in a tendency for the claw tips 48 to wedge or interlock and affect the operation of the grasping head 44.

More particularly, the direct engagement of the closure sleeve 56 with the claw tips 48 forces the tips 48 into a sufficiently tight engagement with each other as to prevent, or at least detrimentally affect the automatic spring-biased opening of the claws 46 as the closure sleeve 56 is retracted. This is clearly an unacceptable situation in the environment of the invention.

The desired forwardmost positioning of the distal end 70 of the closure sleeve 56 is defined by the abutment-forming cross piece or crossbar 36 of the top wall 34 against which the control knob 58 forwardly engages. The retraction of the control knob 58, and hence the closure sleeve 56, is also limited as shall be described subsequently.

While the exposure of the claw tips 48 in the closed position of the grasping head 44 is highly desirable, in assuring proper operation of the claws 46, this does give rise to a substantial problem during passage through the interior of the scope or the working channel therethrough. Basically, the exposed forward or tip portions 48 of the claws 46, even in the closed position of the grasping head 44, will tend to both damage the interior of the scope, and themselves become damaged by engagement with the interior of the scope. This again, in view of the nature of the instrument and its intended use, is unacceptable. Accordingly, the present invention proposed a unique means for protection of both the scope and the grasping head 44 during positioning of the instrument, particularly as it passes through the working channel of the scope, without in any manner interfering with the desired and normal operation of the grasping claws 46.

Figure 2:
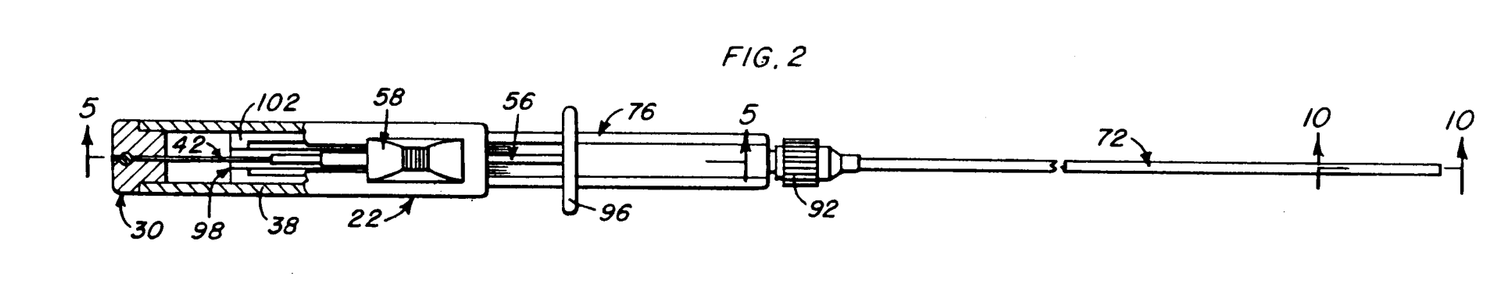
FIG. 2 is a top plan view of the forceps in its fully closed position and with a portion of the handle partially in section.

More particularly, the closure sleeve 56 is surrounded by an elongate sheath 72 with the distal end portion 74 thereof extendable to overlie and enclose the projecting forward tip portions 48 of the collapsed claws 46 as best illustrated in FIGS. 2 and 10. Noting FIG. 10 in particular, the internal diameter of the sheath 72 is greater than the external diameter of the closure sleeve 56 for free sliding movement therebetween. As such, the internal diameter of the distal end portion 74 of the sheath 72 is capable of enveloping or completely enclosing the claws 46 while accommodating the tip portions, slightly spread even in the collapsed position thereof, without a compression of these tip portions as might effect an undesirable wedging or locking thereof. Incidentally, in reference to the sheath 72 completely enclosing the claws, this is intended to describe the position of the sheath when the open leading or distal end 74 thereof is positioned sufficiently beyond the claw tips 48 so as to avoid any possibility of engagement of these tips with the scope as the instrument passes through the working channel of the scope.

The proximal end of the sheath 72 is received longitudinally within and mounted for longitudinal reciprocation by an elongate slide 76.

Figures 6, 7, 8:
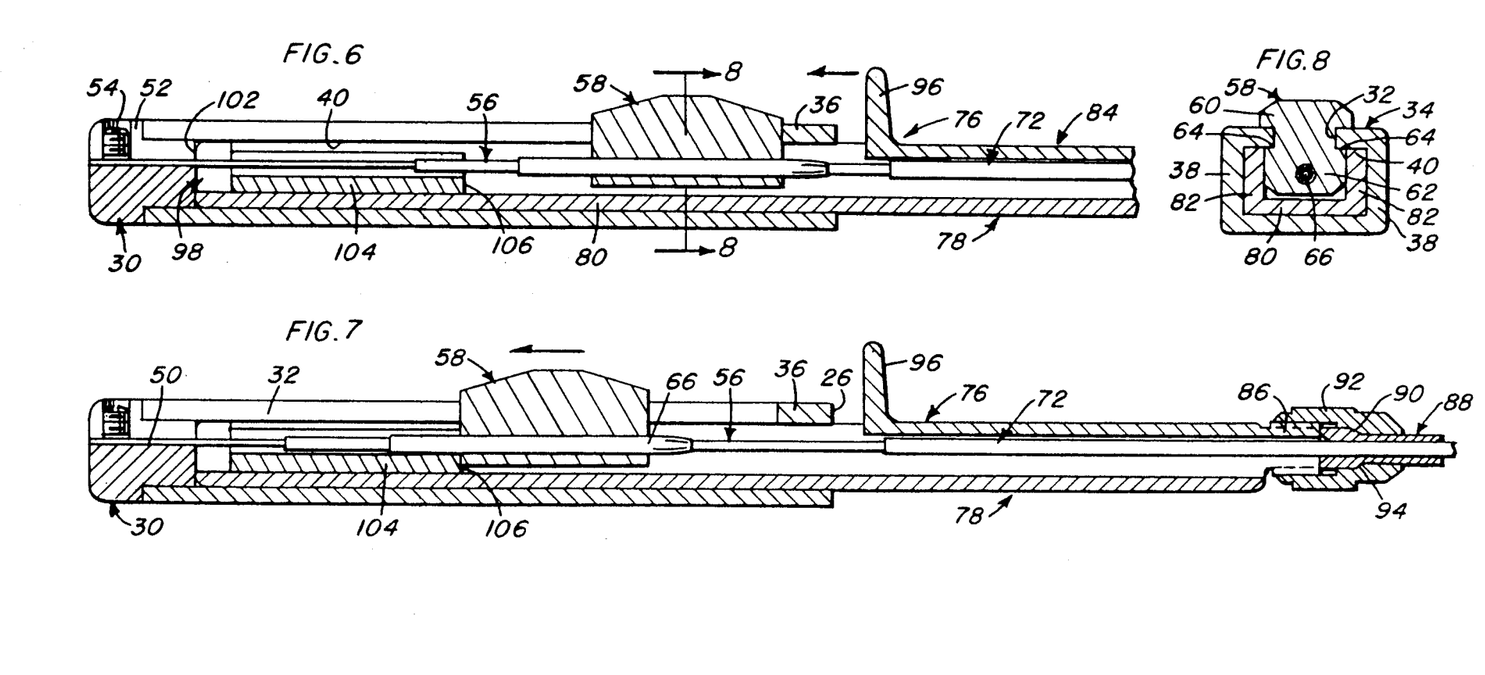
FIG. 6 is an enlarged cross-sectional detail taken substantially on a plane passing along line 6—6 in FIG. 3.
FIG. 7 is a cross-sectional detail taken substantially on a plane passing along line 7—7 in FIG. 4.
FIG. 8 is a cross-sectional detail taken substantially on a plane passing along line 8—8 in FIG. 6.

The slide 76 includes an elongate channel-shaped base or base housing 78. The slide base 78 is approximately twice the length of the handle 22 and is defined by a bottom wall 80 and opposed side walls 82. The rear approximately one half of the slide base 78 is telescopically slidable within the handle 22 through the open forward end 26 thereof. Within the handle 22, and as best noted in FIG. 8, the bottom wall 80 and side walls 82 of the slide base or housing 78 are of a size for intimate sliding engagement with the side walls 38 and bottom wall of the handle 22 immediately inward thereof and in surrounding relation to the control knob body 62. The upper edges of the opposed side walls 82 of the slide housing slidably engage the overlying shoulders 40 defined by the top wall 34 of the handle 22 to the opposite sides of the longitudinal slot 32 therein. The slotted top wall 34 of the handle 22 thus retains both the slide 76 and the control knob 58 for longitudinal reciprocation relative to the handle 22.

The slide 76, immediately forward of the open forward end 26 of the handle 22, includes a top panel 84 welded or otherwise secured between the top edges of the side walls 82 for closing the open top of the slide channel. The panel 84 terminates in a forwardly extending externally threaded neck portion 86 position generally coaxial with the hollow interior of the slide housing 78.

The sheath 72, immediately forward of the neck portion 86, has a sheath seat 88 thereabout and adhesively or otherwise positively affixed thereto. The sheath seat 88 includes a conically configured forwardly directed camming surface 90. The sheath seat 88, and hence the sheath 72 itself, is affixed to the forward end of the neck or neck portion 86 by a retainer or a retaining collar 92 which is received over the sheath seat 88 and is threaded or otherwise fitted onto the neck 86 to rearwardly engage and clamp the seat 88 against the leading end of the neck 86. This is effected by an internal conical bearing surface 94 on the retainer 92 which engages against the seat surface 90 for a clamping bias of the seat 88 against the leading end of the neck as well as toward the sheath 72 to enhance the engagement therebetween. When thus mounted, movement of the slide 76 effects a simultaneous movement of the sheath 72.

The actual manipulation of the slide 76, and hence the sheath 72, is effected by a finger-manipulating plate 96 integral with and projecting laterally from the inner end of the top panel 84. This finger plate 96 is wider than the slide housing 78 and extends vertically along the side walls 82 immediately outward thereof as will be best noted in FIG. 1.

The inner or proximal end of the slide 76 includes an end wall 98 with a central slot 100 therethrough for the accommodation of the cable or shaft 42. The slot 100 extends from the bottom wall 80 through the top of the end wall 98, to define a pair of laterally spaced end wall sections 102. In the rearmost retracted position of the slide 76, and hence the sheath 72, as illustrated in FIGS. 3, 4, 6, 7, the rear end wall 98 of the slide 76 abuts against the inner end of the rear plug cap 30.

An elongate stop member 104 is fixed within the rear portion of the slide housing 78 and extends forwardly from the rear wall 98, terminating in a forward abutment face or end 106 which in turn constitutes a stop against which the control knob 58 engages in its rearmost retracted position. The member 104 has a full length upwardly directed channel 108 defined therein and in generally coaxial alignment with the slide 76 and handle 22 for the free accommodation of both the cable 42 and closure sleeve 56 for free relative movement therebetween.

The abutment face 106 of the stop member 104, when the slide 76 is fully retracted, defines the rearmost position of the control knob 58 as it retracts. This in turn defines the retracted position of the closure sleeve 56. This relationship will best be noted in FIGS. 4 and 7. As previously indicated, the forwardmost position of the control knob 58 and hence the closure sleeve 56 is defined by abutment of the control knob against the forward cross bar member 36 of the top wall 34, note FIGS. 3 and 6.

Figure 5:
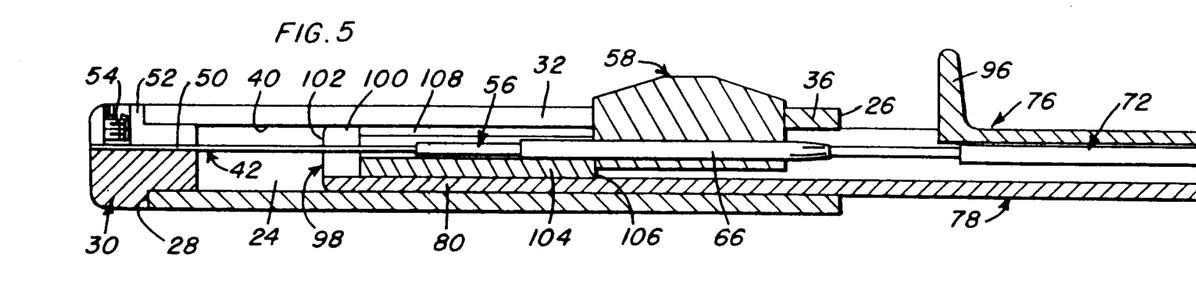
FIG. 5 is an enlarged sectional detail taken substantially on a plane passing along line 5—5 in FIG. 2.

The forwardmost position of the protective sheath 72, enclosing both the closure sleeve and the collapsed although protruding claw tip portions 48, is defined by engagement of the forward abutment end 106 of the stop member 104 against the control knob 58 as it in turn is engaged against the cross member 36, note FIGS. 2 and 5.

Because of the relationship between the stop member 104 and the control knob 58, a forward extension of the sheath so as to enclose the grasping head 44 will, through engagement of the stop member abutment face 106 with the control knob 58, always insure that the closure sleeve is in its forwardmost claw-collapsing position when the sheath is extended. Similarly, retraction of the closure sleeve 56 through a rearward movement of the control knob 58 will, by engagement against the abutment face 106 of the stop member 104, simultaneously effect a rearward movement of the sheath for exposure of both the forward portion of the closure sleeve 56 and the grasping head 44 as the claws move to the open position. In actual use, the manipulation of the components will normally involve sequential operation. More particularly, the instrument, prior to use, will be oriented with both the slide 76 and the control knob 58 in their forwardmost positions, thus both collapsing the grasping head 44 and completely enclosing the claws, note in particular the sectional detail of FIG. 10. As illustrated in this figure, the extended closure sleeve 56 terminates short of the leading end portions of the claws 46 whereby the claws 46 are collapsed into general axial alignment with the closure sleeve 56 without such a compressing and interlocking of the leading tips 48 as might preclude free resilient opening of the claws upon retraction of the closure sleeve. The leading portion 74 of the sheath 72 is positioned with the leading end beyond the collapsed grasping claws 46 so as to completely envelope and enclose the claws. As will be appreciated, the internal diameter of the sheath 72, which is greater than the external diameter of the closure sleeve 56, is also sufficient so as to freely move over the collapsed claws 46 without exerting an additional collapsing or compressing force thereon such as might interfere with their operational control solely by the closure sleeve 56.

When positioned as detailed in FIG. 10, the leading end of the forceps is protected for non-damaging introduction through the working channel 110 of a ureteroscope 112 or the like as schematically illustrated in FIG. 10. The enclosing of the collapsed yet freely expandable claws by the forwardly projecting sheath protects both the tips of the forceps and the working channel of the scope, thus providing a significant dual function.

Once the sheath-protected distal end of the forceps protrudes from the body-received inner end of the scope 112, the sheath is held stationary and the closure sleeve and claws are advanced to expose both the claw-collapsing closure sleeve and the leading tip ends of the collapsed claws. The claws 46 can then be opened and closed through a manipulation of the closure sleeve 56 and without varying the axial position of the grasping head relative to the handle 22, the end of the sheath, or the scope's objective lens (not shown). This helps the user of the device to capture the target, whether a stone, stent, or tissue clump. Further, with the opening and closing of the claws 46 accomplished by the closure sleeve 56 sliding longitudinally forward and rearward relative thereto about the claw-mounting cable or shaft, the claws 46 are capable of closing down on and around the target object without also simultaneously pulling away from the target object, a highly desirable feature in the environment of the invention.

Figure 11:
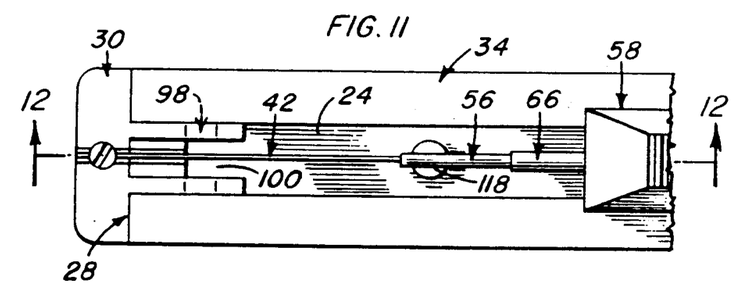
FIG. 11 is a plan view of a portion of a modified form of a forceps handle with means for selectively fixing the position of the sheath.
Figure 12:
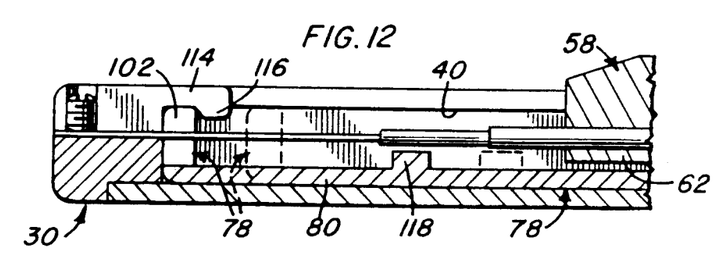
FIG. 12 is a cross-sectional detail taken substantially on a plane passing along line 12—12 in FIG. 11.

With reference to FIGS. 11 and 12, the present invention also contemplates an embodiment wherein the slide 78, and hence the sheath 72, is releasably locked in its rearmost retracted position. This is effected by a pair of spring fingers 114, preferable integrally formed with the end plug closure 30 and projecting inwardly therefrom into the handle slot 32 in the upper wall 34. The fingers 114 will preferably be substantially coplanar with the upper wall 34 and adjacent the opposed edges of the slot. The inner ends of the fingers 114 each include a depending tip 116 projecting into the handle chamber 24 below the upper wall 34 and into the path of rearward movement of the rear end wall 98 of the slide body 80.

The rear wall 98 and in particular the opposed vertical portions 102 thereof to the opposite sides of the central slot 100, upon a retraction of the slide 76, snap behind and are confined by the finger tips 116. This snap-engagement is facilitated by a resilient flexing of the fingers 114 and round corners on both the tips 116 and end wall 98. It is preferred that the wall-accommodating space between the tips 116 and the forward end of the closure plug 30 be such as to closely receive the end wall 98 whereby, when confined, the slide and sheath are fixed until moved by positive manual pressure.

FIGS. 11 and 12 are also of interest in illustrating a modified form of stop member 118 in the nature of a vertically upstanding cylindrical or other shaped projection integral with the bottom wall 80 of the slide housing 78, as opposed to the extended stop member 104 of the first-described embodiment.

Figure 13:
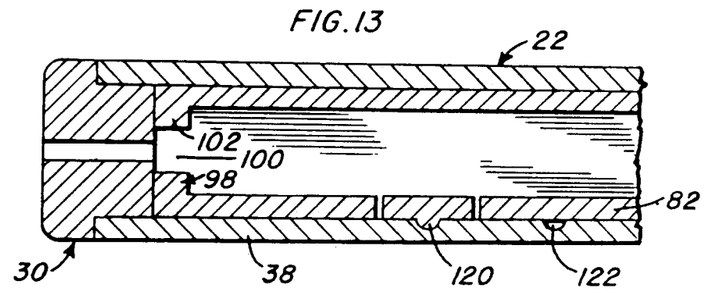
FIG. 13 is a cross-sectional detail of another means for releasably fixing the position of the sheath.
Figure 14:
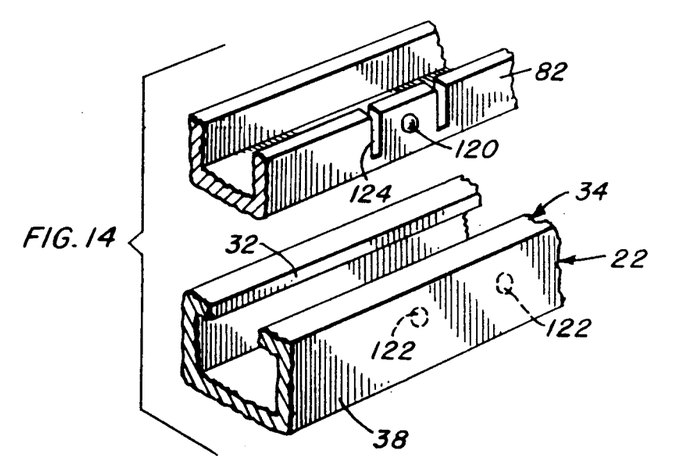
FIG. 14 is an exploded perspective detail of the construction of FIG. 13.

FIGS. 13 and 14 illustrate another means for releasably retaining the slide, and hence the sheath affixed thereto, in both its extended and retracted positions within the handle 22. This is achieved by a locating means comprising a projection 120, of rounded or tapered configuration, extending from the outer surface of one of the slide side walls 82, and a pair of depressions or recesses 122 in the inner surface of a corresponding side wall 38 of the handle 22. The depressions 122 are spaced so as to, upon reception of the projection 120, define the two extreme positions of the slide. In order to facilitate movement of the projection into and out of the recesses 122, as well as along the handle therebetween, the side wall 82, to the opposite sides of the projection 120 can be provided with vertical slots 124 whereby that portion of the wall containing the projection 120 will have an added degree of flexure.

Yet another variation is illustrated in the detail of FIG. 15 wherein both of the opposed side walls 82 of the slide 76 include projections 126 for selective reception within a pair of recesses 128 in the side walls 38 of the handle 22. In this embodiment, the projections 126 move between a position forward of the forward end 26 of the handle and a retracted position, in through the forward end 26 and into releasable locking engagement within the recesses 128. The projection and recess arrangement can, as will be appreciated, constitute a single projection and single cooperating recess, or multiple projections and recesses. Similarly, the projections and recesses, in addition to being located on the side walls, can also, or as an alternative, be located on the cooperating bottom walls of the slide and handle. In each case, in the retracted position of the slide, the rear wall 98 of the slide will preferably abut against the inner end of the end closure plug 30 either with or without the use of the retention or positioning means, as in FIGS. 11-15, for the releasible locking of the slide and sheath in the retracted position.

The rectangular configuration of the handle is significant in facilitating a positive gripping and handling of the device in one hand for ease of manipulation and control with the handle cradled within the palm, the thumb engaged with the control knob 58 and one or two fingers engaged with the push plate 96.

The various components of the forceps are to be formed of appropriate material capable of withstanding standard medical sterilization, for example stainless steel for the closure sleeve, ethylene tetrafluoroethylene plastic for the sheath, and acrylonitrile-butadiene-styrene for the handle and slide.

We claim:

1. A forceps comprising a handle, an elongate flexible shaft extending longitudinally from said handle, said shaft including a forward distal end with multiple claws diverging forwardly and terminating in radially spaced free ends to define an open position, said claws being resiliently moveable radially inward to a closed position wherein the claws are in substantially longitudinal alignment with the shaft, a closure sleeve extending forwardly of said handle and including a distal end for moving said claws to the closed position, said closure sleeve being closely received about and longitudinally reciprocal on said shaft between a retracted position rearward of said claws allowing resilient expansion of said claws to the open position, and an extended position engaged with and inwardly biasing said claws to the closed position, a sleeve control on said handle engaged with and for reciprocation of said closure sleeve between the retracted and extended positions thereof, a protective sheath extending forwardly of said handle and directly received about and longitudinally reciprocal on said closure sleeve between a retracted position rearward of said claws and the sleeve distal end, and an extended position forward of the sleeve distal end for enclosing and forwardly projecting beyond said claws and the free ends thereof, and sheath control means on said handle engaged with and for longitudinal reciprocation of said protective sheath between the retracted and extended positions thereof, and positioning means for automatically moving said closure sleeve to the extended position thereof in response to movement of the protective sheath to its extended position, and for automatically moving said protective sheath to its retracted position in response to movement of said closure sleeve to its retracted position, whereby enclosure of said claws by said sheath occurs only in the closed position of said claws.

2. A forceps comprising a handle, an elongate flexible shaft extending longitudinally from said handle, said shaft including a forward distal end with multiple claws diverging forwardly and terminating in radially spaced free ends to define an open position, said claws being resiliently moveable radially inward to a closed position wherein the claws are in substantially longitudinal alignment with the shaft, a closure sleeve with a distal end for moving said claws to the closed position, said closure sleeve being closely received about and longitudinally reciprocal on said shaft between a retracted position rearward of said claws allowing resilient expansion of said claws to the open position, and an extended position engaged with and inwardly biasing said claws to the closed position, a sleeve control on said handle for reciprocation of said closure sleeve between the retracted and extended positions thereof, said distal end of said closure sleeve, in the extended position thereof, terminating rearwardly spaced from and out of direct contact with the free ends of the claws, a protective sheath received about and longitudinally reciprocal on said closure sleeve between a retracted position rearward of said claws and the sleeve distal end, and an extended position enclosing and forwardly projecting beyond said claws and the free ends thereof, sheath control means on said handle for longitudinal reciprocation of said protective sheath between the retracted and extended positions thereof, said sheath, in the extended position thereof, surrounding the claw free ends without end-compressing engagement therewith, and positioning means for automatically moving said closure sleeve to the extended position thereof in response to movement of the protective sheath to its extended position, and for automatically moving said protective sheath to its retracted position in response to movement of said closure sleeve to its retracted position, whereby enclosure of said claws by said sheath occurs only in the closed position of said claws.

3. The forceps of claim 2 wherein said handle includes a distal end and a proximal end, said handle defining a longitudinally extending interior chamber opening through the distal end thereof, said shaft being longitudinally received within said chamber through the distal end of the handle and into fixed engagement with said handle at the proximal end, said closure sleeve extending into said handle chamber through the distal end of the handle, said sleeve control comprising a control knob engaged with that portion of the closure sleeve within the chamber, said handle including an elongate slot therein communicating with a length of said chamber, said control knob extending through said slot for external access thereto for a manual manipulation thereof, and means mounting said control knob on said housing for longitudinal reciprocation.

4. The forceps of claim 3 wherein said sheath control means comprises an elongate slide longitudinally received within said handle chamber through the distal end thereof, said slide extending longitudinally beyond said handle and terminating in a distal end, said shaft, closure sleeve and sheath being longitudinally received through said slide, said slide, within said handle chamber, having an opening defined longitudinally therealong corresponding to the handle slot for accommodation of the control knob therethrough and into engagement with the closure sleeve within said slide, said longitudinal opening providing for longitudinal reciprocation of the control knob relative to the slide, and sheath retaining means on the distal end of the slide fixing the sheath to the slide for control thereby.

5. The forceps of claim 4 wherein said handle, to the opposite sides of the longitudinal slot therein, defines a pair of shoulders inwardly directed toward the handle chamber, said shoulders confining said control knob and slide against lateral withdrawal from said handle and for longitudinal movement within the chamber.

6. The forceps of claim 5 wherein said control knob includes a portion slidably received within said slide, said positioning means comprising an abutment fixed to said slide rearward of said control knob and selectively engageable by and with said control knob whereby rearward movement of the control knob relative to the slide is limited by engagement with the abutment, and whereby forward movement of the slide is limited by engagement of the abutment with the control knob.

7. The forceps of claim 6 including lock means for releasably locking the slide and sheath in the retracted position thereof, said control knob and closure sleeve being selectively retractable and extendable relative to the locked slide and sheath.

8. The forceps of claim 7 including means for releasably locking the slide and sheath in the extended position thereof.

9. The forceps of claim 7 wherein said handle and said slide include at least one cooperating projection and recess which releasably engage in the retracted position of the slide and constitute the lock means releasably locking the slide and sheath in the retracted position.

10. The forceps of claim 9 wherein said projection and recess comprise end wall means on said slide terminating in a free upper edge, and finger means on the proximal end of the handle, said finger means extending forwardly and terminating in laterally directed tip means in the path of said end wall means upon movement of the slide, said finger means being laterally flexible for passage of the slide end wall means rearwardly past and into engagement behind said tip means.

11. The forceps of claim 9 wherein said at least one projection and recess comprise a laterally directed projection and a cooperating recess on said handle and said slide, one of said handle and said slide incorporating a sufficient degree of flexure as to allow for selective engagement and disengagement of the projection and recess.

12. The forceps of claim 7 including a laterally directed finger-engageable plate rigid with said slide forward of the distal end of the handle for manipulation of the slide and sheath relative to the handle.

13. The forceps of claim 12 wherein said handle has an external rectangular configuration, said handle chamber and said slide having complementary rectangular configurations for a non-rotatable mounting of said slide within said handle chamber.

14. The forceps of claim 4 wherein said handle has an external rectangular configuration, said handle chamber and said slide having complementary rectangular configurations for a non-rotatable mounting of said slide within said handle chamber.

15. A forceps comprising a handle, an elongate flexible shaft extending longitudinally from said handle, said shaft including a forward distal end with multiple claws diverging forwardly and terminating in radially spaced free ends to define an open position, said claws being resiliently moveable radially inward to a closed position wherein the claws are in substantially longitudinal alignment with the shaft, a closure sleeve with a distal end for moving said claws to the closed position, said closure sleeve being closely received about and longitudinally reciprocal on said shaft between a retracted position rearward of said claws allowing resilient expansion of said claws to the open position, and an extended position engaged with and inwardly biasing said claws to the closed position, a sleeve control on said handle for reciprocation of said closure sleeve between the retracted and extended positions thereof, said distal end of said closure sleeve, in the extended position thereof, terminating rearwardly spaced from and out of direct contact with the free ends of the claws, a protective sheath received about and longitudinally reciprocal on said closure sleeve between a retracted position rearward of said claws and the sleeve distal end, and an extended position enclosing and forwardly projecting beyond said claws and the free ends thereof, sheath control means on said handle for longitudinal reciprocation of said protective sheath between the retracted and extended positions thereof, said sheath, in the extended position thereof, surrounding the claw free ends without end-compressing engagement therewith, said handle including a distal end and a proximal end, said handle defining a longitudinally extending interior chamber opening through the distal end thereof, said shaft being longitudinally received within said chamber through the distal end of the handle and into fixed engagement with said handle at the proximal end, said closure sleeve extending into said handle chamber through the distal end of the handle, said sleeve control comprising a control knob engaged with that portion of the closure sleeve within the chamber, said handle including an elongate slot therein communicating with a length of said chamber, said control knob extending through said slot for external access thereto for a manual manipulation thereof, and means mounting said control knob on said housing for longitudinal reciprocation, said sheath control means comprising an elongate slide longitudinally received within said handle chamber through the distal end thereof, said slide extending longitudinally beyond said handle and terminating in a distal end, said shaft, closure sleeve and sheath being longitudinally received through said slide, said slide, within said handle chamber, having an opening defined longitudinally therealong corresponding to the handle slot for accommodation of the control knob therethrough and into engagement with the closure sleeve within said slide, said longitudinal opening providing for longitudinal reciprocation of the control knob relative to the slide, and sheath retaining means on the distal end of the slide fixing the sheath to the slide of control thereby.

16. The forceps of claim 15 including lock means for releasably locking the slide and sheath in the retracted position thereof, said control knob and closure sleeve being selectively retractable and extendable relative to the locked slide and sheath.

* * * * *